United States Patent [19]

Coupland et al.

[11] 4,250,045
[45] Feb. 10, 1981

[54] POLYMERIZED FATTY ACID AMINE DERIVATIVES USEFUL AS FRICTION AND WEAR-REDUCING ADDITIVES

[75] Inventors: Keith Coupland, Sarnia; Clinton R. Smith, Camlachie, both of Canada

[73] Assignee: Exxon Research & Engineering Co., Florham Park, N.J.

[21] Appl. No.: 51,040

[22] Filed: Jun. 22, 1979

[51] Int. Cl.$^3$ .............................................. C10M 1/48
[52] U.S. Cl. .................................. 252/32.7 E; 252/50
[58] Field of Search ............................ 252/32.7 E, 50

[56] References Cited

U.S. PATENT DOCUMENTS

| | | | |
|---|---|---|---|
| 2,898,295 | 8/1959 | MacKenzie | 252/50 X |
| 3,010,782 | 11/1961 | McCaleb | 252/390 X |
| 3,223,631 | 12/1965 | Morway et al. | 252/50 X |
| 3,723,316 | 3/1973 | Massie | 252/50 |
| 3,814,212 | 6/1974 | Latos | 252/50 X |
| 3,933,659 | 1/1976 | Lyle et al. | 252/32.7 E |
| 4,082,518 | 4/1978 | Holtz et al. | 252/50 X |
| 4,089,792 | 5/1978 | Lowe | 252/32.7 E |

*Primary Examiner*—Andrew Metz
*Attorney, Agent, or Firm*—Roland A. Dexter; John J. Mahon

[57] ABSTRACT

A hydrocarbon composition having a major portion of a hydrocarbon preferably a lubricating oil such as mineral oil and at least a friction-reducing amount usually 0.01 to 10 weight percent of an amine or amine derivative of a hydrocarbon-soluble polymerized fatty acid e.g. a dimeramine derived from a dicarboxylic acid containing at least 12 carbon atoms such as 9(10)-carboxy stearic acid has improved antifriction and fuel economy properties.

6 Claims, No Drawings

POLYMERIZED FATTY ACID AMINE DERIVATIVES USEFUL AS FRICTION AND WEAR-REDUCING ADDITIVES

BACKGROUND OF THE INVENTION

The present invention relates to hydrocarbon-soluble amines and amine derivatives of high molecular weight carboxylic acids as an additive for hydrocarbon compositions such as gasoline, fuel oil and lubricating oils including greases, industrial oils, gear oils and lubricants for engines and other equipment having moving parts operating under boundary lubricating conditions so as to improve the antifriction property of said composition.

There are many instances, as is well known, particularly under "Boundary Lubrication" conditions where two rubbing surfaces must be lubricated, or otherwise protected, so so to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

Additives reduce friction between lubricated, moving, metal parts have the propensity to improve fuel economy in the gasoline engine. The mechanism by which this is achieved is conjectured to be by reduction of friction attendant to said moving parts as between, for example, the piston rings and cylinder wall in the engine. If friction can be reduced in the engine, more energy, provided by the fuel, is available to do useful work. In order for an additive to function, it must be delivered to the friction-inducing surfaces efficiently. This can be achieved by incorporating a friction-reducing additive in the lubricant or in the fuel.

Although many classes of compounds work as friction-reducing additives, it is possible to categorize them as either ashless and metal containing. The predominant additives in the metal-containing class are compounds of molybdenum. In the ashless category, many different chemical classes are disclosed such as is taught in U.S. Pat. No. 4,105,571 which although particularly directed to lubricating compositions containing an ester of a polycarboxylic acid with a glycol (the antifriction additive) reports of other ashless additives (see column 1, lines 57 to col. 2, line 8 wherein it is stated "Additive mixtures . . . valve lifter wear . . ." The key features of these materials is oil solubility, minimum interaction with other components of the lubricant formulation, efficiency of action and minimum contribution to the total cost of the oil.

Hydrocarbon-soluble carboxylic acids such as the above-referenced dimer acids are thus well known as are the amines or amine derivatives thereof (see the monograph "The Dimer Acids" edited by E. C. Leonard and published by Humko Sheffield [1975] of Memphis, Tenn. and U.S. Pat. Nos. 2,526,044, 3,223,631 and 3,010,782.

In light of the foregoing, the need for improved lubricating compositions that will permit operation of moving parts under boundary conditions with reduced friction is believed to be readily apparent. Similarly, the need for such a composition that can include conventional base oils and other conventional additives and can be used without the loss of other desirable lubricant properties, particularly those provided by zinc dialkyl dithiophosphates, is also readily apparent.

SUMMARY OF THE INVENTION

It has now surprisingly been discovered that the foregoing and other disadvantages of the proir art lubricating additives and lubricating compositions formulated therewith can be overcome by the presence of at least a friction-reducing amount, generally from 0.01 to 10 weight percent, of an amine or amine derivative of a hydrocarbon-soluble polymerized fatty acid, particularly the class of dimeramines derived from dicarboxylic acids containing at least 12, preferably from 19 to 60, carbons.

In accordance with the present invention, the foregoing and other objects and advantages are accomplished with a hydrocarbon composition comprising a major portion of a hydrocarbon e.g. a lubricating oil and at least a friction-reducing amount of said amine or amine derivative of a hydrocarbon-soluble polymerized fatty acid containing at least 12 carbons, and, if desired, at least a sludge-dispersing amount of an oil-soluble dispersant e.g. an ashless dispersant and at least a rust-inhibiting amount of a rust inhibitor. In practice, the lubricity enhancing additive is present in an amount ranging from 0.01 to 10, preferably 0.05 to 0.5, optimally about 0.1, wt.%, all weight percent being based on the total weight of the oil composition.

DETAILED DESCRIPTION OF THE INVENTION

As discussed above, this invention comprises a high molecular weight nitrogen-containing additive derived from a polymerized fatty acid for lubricants and fuels wherein the improved lubricity property of the hydrocarbon can be from the presence of 0.01–10% additive by weight. The additives are known, commercially available and manufactured by known methods which does not form part of this invention. Typical methods for preparation of the additive involve the conversion of carboxylic acids to the corresponding nitrile followed by reduction to the amine. Further reactions of the amine, also by known methods, with acrylonitrile gives the corresponding cyanoethylated amine which is also useful within the scope of the invention. Reduction of the cyanoethylated amine, also by known methods, yields the corresponding aminopropylamine which is also useful within the scope of this invention. Further chain extension by repeating the cyanoethylation and reduction may be carried out. The starting carboxylic acid may contain more than one carboxylic acid group. It may, for example, be dibasic, tribasic or tetrabasic. Particularly useful are dicarboxylic acids.

In order that the finished product is reasonably soluble in fluids, normally used as lubricants or fuels, it is preferred that the starting carboxylic acid contain more than twelve carbon atoms. Particularly useful carboxylic acids contain between 19–60 carbon atoms. Suitable commercially available dicarboxylic acids containing between 19–60 carbon atoms are derivatives of naturallyoccurring unsaturated fatty acids. Typically these reactions are thermal or acid catalyzed dimerization, addition reactions with a substituted reactive monomer such as acrylic acid or carbonylation with carbon monoxide. The starting material for these reactions has usually been the $C_{18}$ unsaturated acids derived from natural sources. These unsaturated fatty acids are commonly found in vegetable or animal fats. A particularly important source of unsaturated fatty acids is tall oil. Reaction of $C_{18}$ fatty acids with carbon monoxide in the presence of a suitable catalyst will give rise to a $C_{19}$ dicarboxylic acid, for example 9(10)-carboxy stearic acid. Likewise, the addition of acrylic acid to the diunsaturated $C_{18}$ fatty acids, e.g. linoleic acid, produces 5(6)-carboxy-4-hexyl-2-cyclohexene-1-octanoic acid. Dimerization of $C_{18}$ fatty acids, e.g. tall-oil fatty acids, produces an important starting material, the $C_{36}$ dimer acids. This material is a mixture of isomeric products comprising monocyclic dicarboxylic acids, bicyclic dicarboxylic acids and acyclic dicarboxylic acids. The possible structures of these dimer acid types are shown below.

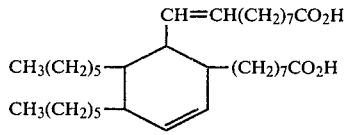

monocyclic

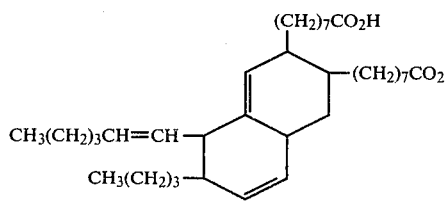

bicycyclic

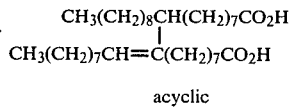

acyclic

For ease of reference, these dicarboxylic structures may be abbreviated to the figure below:

where A is the acyclic or alicyclic diolefin residue from the previous figures.

A further class of dicarboxylic acids is represented by the same general structure but the olefinic unsaturation is removed, or reduced, by hydrogenation. In addition to the $C_{36}$ dicarboxylic acid intermediates, discussed above, lower molecular weight dicarboxylic acids such as the reaction product of tall-oil fatty acids with conjugated unsaturated fatty acids, e.g., acrylic or methacrylic acid.

It is well known, and does not form part of the invention, that the carboxylic acid intermediates can be converted into amines by the following reaction sequence.

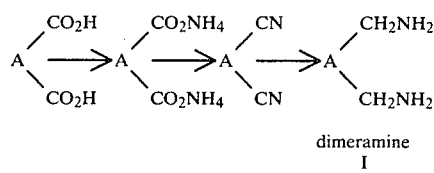

dimeramine
I

This reaction sequence is also described by E. C. Leonard. Compound I is referred to as dimer diprimary amine. It is understood that the reaction sequence above can be readily applied to acids other than the dimer acids.

Further reactions of compound I to provide compounds useful within the scope of the invention are illustrated below:

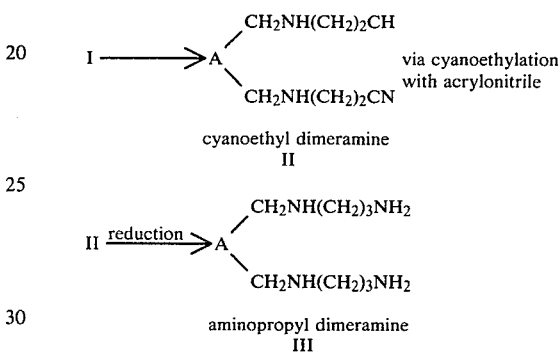

Compound II is referred to as dicyanoethylated dimer diprimary amine. Compound II is referred to as diaminopropyl dimer diprimary amine. The reaction sequences illustrated above for the conversion of I-III can be repeated starting with compound II or III with the production of a homologous series of either polycyanoethylated or polyamino compounds in a cascade reaction.

Suitable dimeramines and dimeramine derivatives are available commercially, for example from Humko Sheffield Chemical of Memphis, Tennessee. The materials are designated Kemamines and typical properties of these amines are listed below.

| Product | Description | Amine Value (min) |
| --- | --- | --- |
| Kemamine DP 3680 | Dimer Diprimary Amine | 175 |
| Kemamine DC 3680 | Dicyanoethylated Dimer Diprimary Amine | 140 |
| Kemamine DD 3689 | Di-N-Aminopropyl Diprimary Amine | 280 |
| Kemamine DP 3695 | Dimer Diprimary Amine | 185 |
| Kemamine DC 3695 | Dicyanoethylated Dimer Diprimary Amine | 140 |
| Kemamine DD 3695 | Di-N-Aminopropyl Diprimary Amine | 230 |

As previously indicated, the amine derivatives of this invention are useful as additives for lubricants in which they function primarily as friction-reducing/fuel economy additives. They can be used in many applications as lubricant compositions in a variety of basestock types. These include natural oils of widely different viscosities, synthetic oils of widely different viscosities and mixtures thereof. The lubricants may be employed as crankcase lubricating oils for spark ignited and compression ignition internal combustion engines. Further, they can find application in two-cycle engines, aviation engines, marine and railroad diesel engines. Other lubricants such as hydraulic fluids, transmission fluids, gear oils and greases are improved by incorporation of the compounds of the present invention.

Natural oils include liquid petroleum oils which may be derived from heavy residuum, coal, shale or reclaimed basestocks. Synthetic oils include hydrocarbons such as polymerized olefins, dibasic acid esters, carboxylic esters of polyhydroxy compounds, polyalkylene oxides, silicones, silicate esters, phosphorus esters, halogenated polymers and mixtures of the above.

Generally the lubricant will contain an amount of the amine derivative sufficient to reduce its coefficient of friction and improve its effect on fuel economy. Normally this amount will be about 0.01–1.00%, preferably 0.02–0.5%. In certain applications, where the lubricating fluid experiences extremely adverse conditions, such as two-cycle oils or marine cylinder lubricants, higher concentrations of up to 10% may be required.

The lubricant composition of the present invention can contain, in addition to the claimed friction modifier, other additives that are normally used in lubricants. Such additives include detergents (e.g. neutral, basic or overbased derivatives of organic acids), viscosity index improvers, rust inhibitors, corrosion inhibitors, defoaming agents, antiwear agents, antioxidants, extreme-pressure agents, pour-point depressants and dispersants. A convenient way of adding the claimed derivatives to the lubricant composition in addition to direct blending is as an admixture with other components normally found in the lubricant. For example, the claimed friction modifier may be added as a dispersant-friction modifier mixture, a zinc dialkyl dithiophosphate (antiwear additive) complex, a solution in the detergent additive, in admixture with the rust inhibitor such as a fatty acid salt or in combination with an antioxidant.

The fuel compositions can contain from about 0.0001% to about 10%, preferably 0.001% to 0.1% of the claimed friction modifier. In addition to the claimed friction modifiers, the fuel can contain other additives commonly found in liquid fuels. These include octane improvers, anti-knock compounds, lead scavengers, cetane improvers, combustion improvers, detergents, dispersants, antioxidants, gum inhibitors, metal deactivators, rust inhibitors, corrosion inhibitors, bacteriostatic compounds and dyestuffs.

The invention will be further understood by reference to the following examples which illustrate a preferred form of the invention and compares the same with different, though similar compositions.

The following examples illustrate more clearly the compositions of the present invention. However, these illustrations are not to be interpreted as specific limitations on this invention.

EXAMPLE 1

Lubricating oil compositions were prepared by blending together the individual components, noted below, usually at a slightly elevated temperature, i.e. from about 45° C. to above 65° C. to insure complete mixing. The final compositions were each formulated into 10W30 SE quality automotive engine oils as follows:

Blends

| | Wt. % Active Ingredient |
|---|---|
| Mineral Oil | 90.5 |
| Ashless Dispersant | 4.1 |
| Magnesium Sulfonate | .3 |
| Zinc dialkyl dithiophosphate | 1.8 |
| Rust-Inhibitor | 0.1 |
| Viscosity Index Improvers | 1.1 |
| Silicone Defoamer | 0.01 |
| Ashless Antioxidant | |
| Metal Detergent-Inhibitor | 2.0 |
| Friction-Reducing Agent | 0.1 |

Six formulated test blends and a control without a friction-reducing agent were subjected to two testing procedures as hereinafter set forth:

TEST METHOD A

A Roxana Four-Ball tester with the Brown/GE modification was used to measure friction by the following procedure. Three one-half inch bearing steel balls HRC 62–64, as described in procedure ASTM D 2266-67 are cleaned by rinsing in a light organic solvent, air dried and placed in the ball pot. A fourth one-half inch ball made of AISI 52100 steel and of hardness RC 20 is soaked in 1 N HCl for 60 seconds, rinsed in water, rinsed in isopropyl alcohol and air dried. This ball is placed in a chuck and mounted on the tester's spindle.

The lubricant (15 ml) is added to the ball pot and the tester is assembled as per the manufacturer's instructions.

A normal load of 15 kg is applied to the balls and the oil is heated to 110° C. After the lubricant is on temperature, the spindle ball is rotated at 2.5 rpm (0.096 cm/sec). The frictional force is measured by a load cell and displayed on a strip chart recorder. These conditions are maintained for 45 minutes after which the load is dropped to 3 kg and the test continued for 15 minutes.

Coefficient of friction is calculated over the last 15 minutes at each load.

TABLE 1

| Example | Additive | Concentration % | Coefficient of Friction 15 kg | Coefficient of Friction 3 kg | Friction Reduction* (%) 15 kg | Friction Reduction* (%) 3 kg |
|---|---|---|---|---|---|---|
| 1 | None | Control- | .16 | .23 | — | — |
| 2A | Kemamine Dp-3680 | 0.1 | .11 | .12 | 31 | 48 |
| 3A | Kemamine DC-3680 | 0.1 | .11 | .11 | 31 | 52 |
| 4A | Kemamine DD-3680 | 0.1 | .10 | .13 | 38 | 43 |
| 5A | Kemamine DP-3695 | 0.1 | .11 | .12 | 31 | 48 |
| 6A | Kemamine DC-3695 | 0.1 | .10 | .11 | 38 | 52 |
| 7A | Kemamine DD-3695 | 0.1 | .10 | .12 | 38 | 48 |

TEST METHOD B

A Chevrolet 305 CID 8-cylinder engine is mounted on a dynamometer such that the engine may be operated under conditions of constant load and speed. Fuel usage is determined using a Fluidyne ® fuel meter. The test procedure involves running the engine at four conditions of speed and load (tabulated below), the fuel consumption is measured at each of the four test conditions and replicated four times. An average fuel usage over the total test conditions is then determined. By comparing the blended test lubricants, each with a fuel economy additive, with the same oil but without the fuel economy additive (reference), the effect of the fuel economy additive may be seen determined as demonstrated in the data of Table 2.

Fuel Economy Engine Test Conditions

| Speed (rpm) | Load (in lb) |
|---|---|
| 800 | 400 |
| 1200 | 450 |
| 1200 | 950 |
| 2200 | 900 |

TABLE 2

| Example | Additive | Concentration | Fuel Economy Improvement (%) |
|---|---|---|---|
| 1 | None | — | 0 (reference) |
| 2.B | Kemamine DP-3695 | 0.3 | 2.32 |
| 3.B | Kemamine DP-3695 | 0.1 | 1.92 |
| 4.B | Kemamine DC-3695 | 0.1 | 2.33 |
| 5.B | Kemamine DP-3695 | 0.1 | 2.53 |
| 6.B | Kemamine DD-3695 | 0.1 | 0.88 |
| 7.B | Kemamine DD-3695 | 0.3 | 1.45 |

From the foregoing, it is shown that the additives of the invention provide lubricity enhancement to lubricating oils.

It is to be understood that the examples present in the foregoing specification are merely illustrative of this invention and are not intended to limit it in any manner; nor is the invention to be limited by any theory regarding its operability. The scope of the invention is to be determined by the appended claims.

What is claimed is:

1. A liquid hydrocarbon lubricating oil composition comprising a major proportion of a liquid hydrocarbon lubricating oil and from about 0.01 to 10 wt. % of a friction-reducing additive, said additive being a hydrocarbon soluble diprimary diamine of a dimerized $C_{19}$-$C_{60}$ fatty acid or derivative thereof, said derivative being a cyanoethylated or amine propylamine derivative.

2. A composition according to claim 1 wherein said hydrocarbon lubricating oil is mineral oil and contains further at least a sludge-dispersing amount of an oil-soluble dispersant and at least a wear-reducing amount of an antiwear additive.

3. A composition according to claim 1 wherein said additive is a dimeramine of a dimerized natural fatty acid and said composition further comprising metal dialkyl dithiophosphate antiwear additive.

4. A composition according to claim 3 wherein said diprimary dimeramine is di-N-(2-cyanoethyl) dimeramine.

5. A composition according to claim 3 wherein said diprimary dimeramine is di-N-aminopropyl diprimary amine.

6. A composition according to claim 3 wherein said natural fatty acids are derived from tall-oil, soybean oil or linseed oil.

* * * * *